United States Patent [19]

Grabner

[11] Patent Number: 4,901,559
[45] Date of Patent: Feb. 20, 1990

[54] METHOD AND ARRANGEMENT FOR MEASURING THE VAPOR PRESSURE OF LIQUIDS

[76] Inventor: Werner Grabner, Nussdorfer Str. 4/11, A 1090 Vienna, Austria

[21] Appl. No.: 302,238
[22] PCT Filed: Jul. 17, 1987
[86] PCT No.: PCT/AT87/00040
  § 371 Date: Dec. 30, 1988
  § 102(e) Date: Dec. 30, 1988
[87] PCT Pub. No.: WO88/00692
  PCT Pub. Date: Jan. 28, 1988

[30] Foreign Application Priority Data

Jul. 18, 1986 [AT] Austria ................. 1961/86

[51] Int. Cl.$^4$ .............................................. G01N 7/14
[52] U.S. Cl. ...................................................... 73/64.2
[58] Field of Search ................................ 73/64.2, 29

[56] References Cited

U.S. PATENT DOCUMENTS

| | | | |
|---|---|---|---|
| 2,995,922 | 8/1961 | Firth et al. | 73/64.2 |
| 3,360,980 | 1/1968 | Webb | 73/29 |
| 3,499,317 | 3/1970 | Hook | 73/64.2 |
| 4,393,689 | 7/1983 | Renon et al. | 73/64.2 |
| 4,543,819 | 10/1985 | Chin et al. | 73/64.2 |

FOREIGN PATENT DOCUMENTS

| | | |
|---|---|---|
| 2474196 | 7/1981 | France . |
| 1026024 | 6/1983 | U.S.S.R. ................. 73/64.2 |
| 1227991 | 4/1986 | U.S.S.R. ................. 73/64.2 |
| 832085 | 4/1960 | United Kingdom . |
| 974183 | 11/1964 | United Kingdom . |

OTHER PUBLICATIONS

Gibbs, R. E. et al., Vapor-Liquid Equilibria from Total-Pressure Meas. In Ind. Eng. Chem. Fund., vol. (11), No. 3, Aug. 1972, pp. 410-413.

Primary Examiner—John Chapman
Assistant Examiner—Joseph W. Roskos
Attorney, Agent, or Firm—Steinberg & Raskin

[57] ABSTRACT

Method for measuring vapor pressure of liquids in which liquid to be measured is placed in a previously-evacuated measuring cell, and influence of the gas dissolved in the liquid on the measuring results is eliminated. The liquid to be measured is added in at least two separate portions, with total pressure present in the measuring cell being measured after the addition of each portion and after saturation vapor pressure equilibrium has become established, to obtain a thus-measured value. Gas pressure present in the measuring cell which is due to the gas dissolved in the liquid is derived from at least two thus-measured values which had been obtained at the same measuring temperature in which pressure components due to vapor pressure of the liquid are equal, taking into account the liquid quantity contained in the particular liquid portions and the measuring cell volume with the relation $po=RT$. The vapor pressure of the liquid is determined by subtracting the derived gas pressure from the total measured pressure. The present invention is also directed to an arrangement for measuring the vapor pressure of liquids, which has a measuring cell and a pressure measuring device connected to the same, as well as to a filling tube and a vacuum connection. The pressure measuring device is connected with the measuring cell through a connecting tube extending nearly to a bottom of the measuring cell. The opening of the connecting tube thereby lies below a liquid level present during the measurement in the measuring cell.

11 Claims, 1 Drawing Sheet

U.S. Patent   Feb. 20, 1990   4,901,559
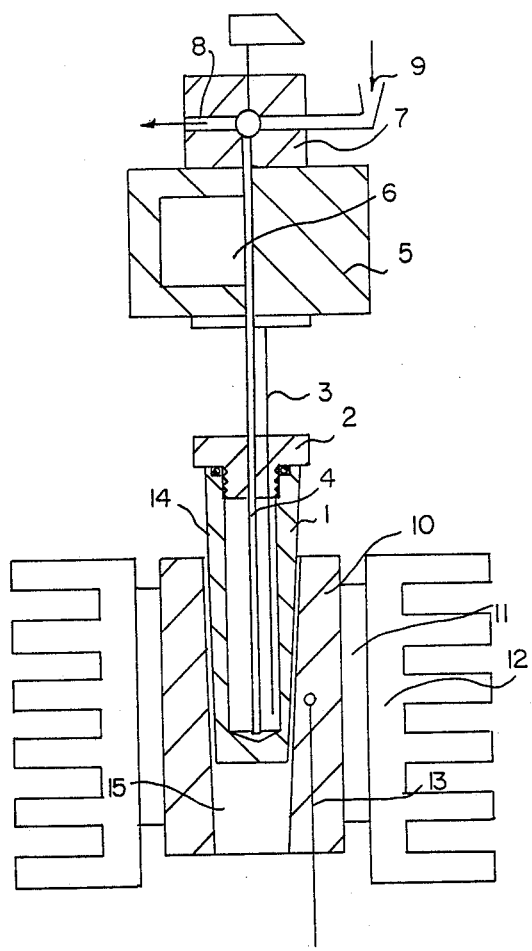

METHOD AND ARRANGEMENT FOR MEASURING THE VAPOR PRESSURE OF LIQUIDS

BACKGROUND OF THE INVENTION

The invention relates to a method for measuring the vapor pressure of liquids in which method the liquid to be measured is placed into a previously evacuated measuring cell and the effect of the gases dissolved in the liquid on the measurement results is excluded. The invention, further, relates to an arrangement for measuring the vapor pressure of liquids.

The vapor pressure of a liquid is that pressure which in a closed system builds up above the liquid; this pressure changes until the vapor is in dynamic equilibrium with the liquid. The then-present pressure is called saturation vapor pressure and this is exclusively a function of the temperature of the system and does not depend on its geometry. The values published in the literature for the vapor pressure of a substance are always saturation vapor pressure values, since only these can be stated specifically for the substance and do not depend on the measuring method. In principle, the measurement of the vapor pressure of a liquid can be carried out so that this liquid is placed into a tightly closable vessel which is provided with a pressure measuring arrangement, the vessel closed, and the pressure present in the vessel is measured. If the quantity of liquid is sufficiently large so that at the measuring temperature in spite of evaporation residual liquid remains in the vessel, the vapor pressure is the saturation vapor pressure. These circumstances, which in principle are simple, are complicated by the fact that the ambient atmospheric pressure and the pressure of the gas dissolved in the liquid to be measured can significantly influence the measurement.

The techniques used until now either accept a falsification of the measured results through the ambient atmospheric pressure and the pressure of the gas dissolved in the liquid, with in some cases the aim being to keep the error approximately the same through standardized procedural specifications in order to be able to compare the measuring results obtained from different liquids (for example vapor pressure determination after Reid), or the aim is with extremely great operation complexity in terms of laboratory means to exclude not only the influence of the ambient atmospheric pressure but also to free the liquid to be tested of the gases dissolved therein before undertaking measurements. With the known techniques particularly great difficulties are encountered if the vapor pressure of mixtures of liquids is to be determined.

In GB-A-832 085 a method for measuring the vapor pressure of liquids is described in which first the liquid to be tested is placed into an evacuated chamber in which grainy material is located in order to make available a large surface. The large surface favors the emergence of gases dissolved in the liquid. Following this pretreatment, the liquid is transferred to a bottle, the evacuated chamber is cleaned, and the liquid is subsequently placed once again into said chamber which thereupon is again evacuated and subsequently closed, whereupon the pressure developing in this chamber is measured. This approach is cumbersome, and in the case of liquid mixtures changes in the composition result through the evacuation. It is in GB-A-832 085 further described that the quantity of a gas contained in a liquid can be determined if the vapor pressure of this liquid can be neglected, in that this liquid is placed into an evacuated chamber in which grainy material is present, and measures the pressure built up in this chamber by the gas emerging from the liquid. From the thereby, obtained measured values for the pressure using the relation $p*v=R*T$, the quantity of the gas which had been present in the liquid relative to normal pressure and normal temperature is calculated.

A method for determining the gas content of a liquid is also described in GB-A-974 183. In this method too, the liquid to be tested is placed into an evacuated chamber, and the pressure originating in this chamber is measured. The volume of the chamber in which the liquid is located is variable by displacing a piston. Two measurements at different positions of the piston are carried out. The measured pressure is composed in each instance from the pressure of the gas and the vapor pressure of the liquid. From two measured pressure values, assuming that the unknown vapor pressure has the same value in both measurements, the gas quantity contained in the liquid is calculated.

SUMMARY OF THE INVENTION

It is a goal of the present invention to create a method for measuring the vapor pressure of liquids which is simple to carry out and which is well suited for industrial application, and in so doing supplies precise measuring results. The invention is further to create an arrangement which permits simple execution of the method according to the invention and permits achieving good measuring accuracy.

The method according to the invention of the initially cited type is characterized in that the liquid to be measured is placed, in two or several portions, into the previously evacuated measuring cell, with the second liquid portion following the first liquid portion or the following liquid portions being in each instance added to the liquid already present in the measuring cell. In each instance after the placing of a portion after the saturation vapor pressure equilibrium has become established, the total pressure present in the measuring cell is measured. From at least two of the measured values obtained in the process at identical measuring temperature, in which the pressure components originating from the vapor pressure of the liquid are equal taking into account the liquid quantities contained in the particular liquid portions and the measuring cell volume using the relation $p*v=R*T$, the vapor pressure present in the measuring cell is derived which stems from the gas which had been dissolved in the liquid to be tested. The vapor pressure of the liquid is determined by subtracting this gas pressure from the measured total pressure. In this way the value of the absolute saturation vapor pressure is obtained.

Through the approach according to the invention the above stated goal can readily be addressed and it is a significant advantage of this method that it also permits precise measurement of the saturation vapor pressure of mixtures of liquids. The method according to the invention is particularly advantageous for measuring the vapor pressure of hydrocarbons which may contain relatively large quantities of dissolved gases, including air.

In the method according to the invention through the addition in portions of the liquid to be measured into the measuring cell and by carrying out at least two measurements at the same temperature, however, at different filling levels of the measuring cell at least two measuring values are formed in which the pressure component formed by the vapor pressure of the liquid in each instance is equally large. Using this specific property of the measured values as basis the pressure component stemming from the gases is derived, and after knowing the latter pressure components the vapor pressure of the liquid can be determined from the total pressure obtained at each measurement.

It is advantageous in the interest of a simple process execution if the liquid to be measured is added to the measuring cell in portions of equal size with respect to each other.

To increase the accuracy of the measuring results it is favorable if for determining the gas pressure, several pressure measurements are carried out, each time at the same temperature.

A very simple derivation of the gas pressure within the scope of the method according to the invention results if the liquid to be measured is added to the measuring cell in two portions of equal size, if the two pressure measurements following the addition of the portions into the measuring cell are undertaken at the same temperature if the gas pressure occurring after the addition of the second liquid portion is determined with the relation $p_G = 2(p_2 - p_1)$, where $p_1$ and $p_2$ are the measured values obtained in the first and the second pressure measurement. To increase the accuracy, a correction factor is to be used in determining the gas pressure which takes into account the compression which originates through the introduction of the additional portion of the liquid to be measured.

A further embodiment of the method according to the invention, which permits in a simple manner, a precise determination of the curve of vapor pressure of liquids over a temperature range, is characterized in that after the measurement undertaken to determine the gas pressure, additional pressure measurements are carried out at different temperatures and for the determination of the vapor pressure of the liquid to be measured obtained at these temperatures, a value of the gas pressure is subtracted from the obtained measured values corrected to the temperature at the particular measurement using the relation $p^*v = R^*T$.

For carrying out the method according to the invention, a simple closable measuring cell can be used which is equipped with a pressure measuring arrangement and which can be brought to predetermined temperatures with a thermostat. After cleaning and evacuating this measuring cell to a final pressure of below 1 hPa by means of an apportioning syringe which can be placed on a filling tube neck of the measuring cell, the first half of the liquid to be measured can be added to the measuring cell. In the measuring cell thereupon a total pressure results which is composed of the vapor pressure of the liquid and the gas pressure of the gases which had been dissolved in the added liquid portion. After the temperature adjustment this total pressure is measured. Subsequently the second half of the liquid is placed into the measuring cell with the apportioning syringe and again temperature adaptation and development of the saturation vapor pressure equilibrium waited for, whereupon again the total pressure obtained in the measuring cell is measured. The second measurement is carried out at the same temperature as the first measurement. Because the temperature is the same, the saturation vapor pressure of the liquid or the component of the total pressure formed by the saturation vapor pressure is the same in both measurements. In the second measurement the gas pressure corresponds to the total quantity of gases which were dissolved in the two liquid portions which were placed into the measuring cell.

Thus, in filling two equal portions of the liquid to be measured into the measuring cell and at the same temperature the following correlations result during the first and the second pressure measurement:

$p_1 = p_{Fl} + p_G(m)$: total pressure in the measuring cell at liquid quantity m $p_2 = p_{Fl} + p_G(2m)$: total pressure in the measuring cell at liquid quantity 2m where $p_{Fl}$: is the vapor pressure of the liquid $p_G(m)$: the gas pressure of the gases which had been dissolved in the liquid quantity m $p_G(2m)$: the gas pressure of the gases which had been dissolved in the liquid quantity 2m.

As a first approximation on the basis of the gas equation $p^*v = R^*T$ at constant temperature $$p_G(2m) = 2(p_G(m))$$

can be set with sufficient accuracy.

If a more precise derivation of the gas pressure is desired, the gas compression occuring upon adding the second liquid portion is taken into account in a correction factor which results from the known volume of the measuring cell and the volume of the added liquid portions.

From the above relation a simple derivation of the gas pressure results as follows:

$$p_2 - p_1 = (p_{Fl} + p_G(2m)) - (p_{Fl} + p_G(m))$$

in which $p_1$ can, as above, be corrected using a correction factor. With:

$$p_G(2m) = 2p_G(m)$$

$$p_2 - p_1 = p_G(2m) - p_G(m)$$

results and $$p_G(2m) = 2(p_2 - p_1)$$

is obtained.

The gas pressure $p_G$ (2m) derived in this manner which stems from the total liquid quantity present in the measuring cell is subtracted from the measured total pressure in order to obtain the vapor pressure $p_{Fl}$ of the liquid.

In analogous manner the liquid to be measured can be placed in more than two portions into the measuring cell and a pressure measurement can be carried out at the same temperature after each portion is added and from these measurements, in a manner analogous to the previously described in conjunction with two pressure measurements, the gas pressure can be derived. The derivation of this gas pressure from more than two measurements is more complex than the derivation from two total pressure measurements described previously. It does, however, permit greater accuracy.

As soon as the gas pressure has been derived, the temperature present in the measuring cell can be changed in order to determine the vapor pressure at any given temperatures. The previously obtained value of the gas pressure for these other measuring temperatures is corrected or converted using the gas equation $p*v=R*T$ and subtracted from the measured total pressure values, in order to obtain the saturation vapor pressure of the tested liquid at the particular measuring temperatures. In this way a complete vapor pressure curve which also detects a greater temperature range can easily be determined.

The arrangement according to the invention for measuring the vapor pressure of liquids, which has a measuring cell and a pressure measuring device connected to this measuring cell as well as a filling tube and a vacuum connection, is characterized in that the pressure measuring device is connected to the measuring cell through a connecting tube reaching nearly to the bottom of the measuring cell, and so the opening of the connecting tube during the measurement lies below the liquid level provided in the measuring cell. This design of the arrangement permits that with very simple structure a good accuracy of the pressure measurements required for the vapor pressure determination can be achieved. The pressure measuring device can be kept separate from the measuring cell at essentially constant operating temperature (in particular at ambient temperature), whereby in a very simple manner impairments of accuracy of the pressure measurement which may originate due to different temperatures at the pressure measuring device are excluded. By virtue of that fact that the connecting tube which leads from the measuring cell to the pressure measuring device opens under the liquid level in the measuring cell, penetration of vapors of the liquid into the connecting tube and into the pressure measuring device is excluded. Therewith falsification of the measured values which may originate through a condensation of these vapors in the connecting line or in the pressure measuring device is prevented.

A preferred embodiment of the arrangement implemented according to the invention which permits a very simple operation of this arrangement is characterized in that to a connecting tube leading from the measuring cell to the pressure measuring device, a selector valve is connected from which extend the filling tube and the vacuum connection.

A very simple structure and also a simple operatability of the arrangement results, if the measuring cell is arranged in a solid phase thermostat. Thereby good heat contact of thermostat to measuring cell and also easy accessibility of the measuring cell during operation is obtained if the measuring cell is conically shaped along its outside in the longitudinal direction and the solid phase thermostat has a metal block which has a bore shaped corresponding to the outside of the measuring cell into which can be disposed the measuring cell.

Further, with very simple constructional setup good settability of the temperature over a very wide temperature range results which reaches from values lying relatively far below the ambient temperature to high temperatures, if provisions are made that the solid phase thermostat has Peltier elements for setting the temperature.

BRIEF DESCRIPTION OF THE DRAWINGS

The invention will now be explained in greater detail with reference to an embodiment example of an arrangement implemented according to the invention and represented in the drawing.

DESCRIPTION OF THE PREFERRED EMBODIMENTS

In the arrangement represented in the drawing, a measuring cell 1 is provided which advantageously consists of stainless and acid resistant special steel. Such a measuring cell may, for example, have a volume of 5 ml and be formed in the shape of a cylinder with an inner diameter of 10 mm. The measuring cell 1 is closed with a sealing cover 2 which can be screwed on, with a sealing ring being advisably inserted between the sealing cover 2 and the measuring cell 1 to provide sealing. Through the sealing cover 2 a temperature sensor 3 is inserted into the interior of the measuring cell 1; such a temperature sensor is advisably arranged in a special steel hollow needle which projects into the liquid in the measuring cell so that the temperature sensor detects precisely the temperature of this liquid. Through the sealing cover 2, further, a connecting tube 4 which is also advantageously implemented in the form of a hollow needle is inserted into the interior of the measuring cell 1 and projects into the bottom area of the measuring cell. The connecting tube 4 leads to a measuring head 5 in which a pressure measuring device 6 is disposed. The pressure measuring device can advantageously be implemented in the form of a piezoresistive pressure transducer which is installed in such a way that the free volume is of minimum size. On the upper side of the measuring head 5 a selector valve 7 is closely placed extending the connecting tube 4, which selector valve is implemented in the form of a three-way ball valve. From the selector valve 7 extend a vacuum connection 8 and a filling tube neck 9. Thus via the selector valve 7 and the vacuum connection 8 the measuring cell 1 can be evacuated, and via the filling tube neck 9 be filled with the liquid to be tested. For filling, for example, an apportioning syringe can be placed in the filling tube neck 9. Thereby that the connecting tube 4 reaches to the bottom of the measuring cell 1, and hence opens below the liquid level present in the measuring cell 1 during operation, penetration of gases from the gas space of the measuring cell into the connecting tube 4 and further to the pressure measuring device 6 can be counteracted and such errors of measurement are avoided which, for example, may result due to the occurrence of condensation phenomena in the area of the connecting tube 4 and in the area of the pressure measuring device 6. The measuring cell 1 is shaped conically at its outside 14 in the longitudinal direction and seats in a correspondingly shaped bore 15 which is provided in a metal block 10, preferably an aluminum block, of a solid phase thermostat. In the metal block 10 for controlling or setting the temperature of the same, a temperature sensor 13 is arranged which controls Peltier elements 11 via a control device not further shown. The Peltier elements 11 are thermally coupled with cooling bodies 12 and permit setting the temperature of the metal block 10 and hence also setting the temperature which obtains in the measuring cell 1 to the particular desired value. With the aid of these Peltier elements the temperature of the metal block 10 can be set in any given way to a value within the range of $-20°$ C. to $150°$ C.

Advantageously an automatic control of the operating processes can be provided with the aid of a control apparatus which sequentially controls the measurements carried out in the course of the filling process taking place by portions and also automatically the derivation of the saturation pressure value from the measurements of the determined total pressure values. In measuring vapor pressure curves with automatic control of the progression of the filling and measuring processes through the thereby given, fixed function progression, the temperature changes can be carried out either in discrete steps or also continuously with settable rate. The measured values can be automatically sensed, stored, and printed out and, as mentioned, from the measured values derive automatically the vapor pressure values and also store and print out the vapor pressure values, if desired. It is also possible to use apparatus which automatically plots curves (plotter) to represent automatically vapor pressure curves.

I claim:

1. Method for measuring vapor pressure of liquid in which liquid to be measured is placed in a previously-evacuated measuring cell and influence of gas dissolved in the liquid on measuring results is eliminated, comprising the steps of adding the liquid to be measured in two or more separate portions into the previously-evacuated measuring cell, measuring total pressure present in the measuring cell following each addition of one portion and after saturation vapor pressure equilibrium has become established, to obtain a thus-measured value, deriving gas pressure present in the measuring cell due to the gas dissolved in the liquid from at least two thus-measured values obtained at the same measuring temperature, in which pressure components due to vapor pressure of the liquid are equal, taking into account liquid quantity contained in the liquid portions and the measuring cell volume and using the relationship $pv = RT$, and determining vapor pressure of the liquid by subtracting the thus-derived gas pressure from the total measured pressure.

2. The method of claim 1, wherein the liquid to be measured is added to the measuring cell in portions which are substantially equal.

3. The method of claim 1, comprising the additional step of carrying out several pressure measurements at the same temperature, to determine the gas pressures.

4. The method of claim 1, wherein the liquid to be measured is placed in the measuring cell in two portions of substantially equal size, and the gas pressure occurring after the addition of the second subsequent liquid portion is determined by the relationship $p_G = 2(p_2 - p_1)$, wherein $p_1$ and $p_2$ are the measured values obtained as the first and second measured values.

5. The method of claim 4, comprising the additional step of, utilizing a correction factor in the determination of the gas pressure, for taking into account compression which occurs in the placing of the additional portion of liquid to be measured in the cell.

6. The method of claim 1, comprising the additional steps of carrying out further pressure measurements at different temperatures, to obtain further measured values, and subtracting from the further measured values that were obtained, a value of gas pressure corrected to the temperature at the particular measurement using the relationship $pv = RT$, for determining the vapor pressure of the liquid at these different tempeatures.

7. Apparatus for measuring vapor pressure of liquids, comprising a measuring cell (1), a pressure measuring device (6) coupled to said measuring cell (1) and to a filling tube (9) and a vacuum connection (8), wherein said pressure measuring device (6) is coupled to said measuring cell (1) through a connecting tube (4) extending near to a bottom of the measuring cell (1), with an opening of said connecting tube (4) arranged to lie below liquid level present in said measuring cell (1) during measurement.

8. The combination of claim 7, additionally comprising a selector valve (7) coupled to said connecting tube (4) extending from said measuring cell (1) to said pressure measuring device (6), such that said filling tube (9) and said vacuum connection (8) both extend from said selector valve (7).

9. The combination of claim 7, additionally comprising a solid phase thermostat in which said measuring cell (1) is arranged.

10. The combination of claim 9, wherein said measuring cell (1) is conically shaped along an outer surface (14) thereof in a longitudinal direction, and said solid phase thermostat comprises a metal block (10) having a bore (15) complementary-shaped to the outer surface of said measuring cell (1), such that said measuring cell (1) can be disposed said thermostat bore (15).

11. The combination of claim 9, wherein said solid phase thermostat comprises Peltier elements (11) for setting the temperature.

* * * * *